(12) United States Patent
Simpson et al.

(10) Patent No.: US 6,447,493 B1
(45) Date of Patent: Sep. 10, 2002

(54) PROTEX PATCH FOR BOYS AND MEN

(76) Inventors: Timothy Rodgrick Simpson, 1040 Rte. 166, Apt. 1501, Toms River, NJ (US) 08753; Nykesha Shameka Simpson, 1040 Rte. 166, Apt. 1501, Toms River, NJ (US) 08753

( * ) Notice: Subject to any disclaimer, the term of this patent is extended or adjusted under 35 U.S.C. 154(b) by 0 days.

(21) Appl. No.: 09/394,254

(22) Filed: Sep. 13, 1999

Related U.S. Application Data

(60) Provisional application No. 60/124,353, filed on Mar. 5, 1999.

(51) Int. Cl.[7] .............................................. A61K 13/15
(52) U.S. Cl. ................... 604/385.03; 604/349; 604/387
(58) Field of Search ................................ 604/390, 386, 604/387, 389, 385.03, 385.05, 385.14, 402, 347, 349

(56) References Cited

U.S. PATENT DOCUMENTS

| | | | | |
|---|---|---|---|---|
| 4,064,880 A | * | 12/1977 | Logan ......................... 128/294 |
| 4,505,707 A | * | 3/1985 | Feeny ......................... 604/393 |
| 4,559,051 A | * | 12/1985 | Hanson ................... 604/385 R |
| 4,576,599 A | * | 3/1986 | Lipner ........................ 604/390 |
| 4,666,229 A | * | 5/1987 | Fago et al. .................. 604/337 |
| 4,668,229 A | * | 5/1987 | Fago et al. .................. 604/327 |
| 4,795,450 A | * | 1/1989 | Tovar et al. ................. 604/349 |
| 4,863,448 A | * | 9/1989 | Berg ........................... 604/349 |
| 4,886,509 A | * | 12/1989 | Mattsson ..................... 604/349 |
| 5,037,418 A | * | 8/1991 | Kons et al. .................. 604/387 |
| 5,695,485 A | * | 12/1997 | Duperrt et al. ............. 604/349 |
| 5,702,381 A | * | 12/1997 | Cottenden ................ 604/385.1 |
| 6,013,066 A | * | 1/2000 | Samuelson ................... 604/387 |
| 6,061,839 A | * | 5/2000 | Smolik .......................... 2/400 |

FOREIGN PATENT DOCUMENTS

WO    WO 89/00037    * 12/1999

* cited by examiner

*Primary Examiner*—John G. Weiss
*Assistant Examiner*—Michael G. Bogart
(74) *Attorney, Agent, or Firm*—Akin, Gump, Strauss, Hauer & Feld, L.L.P.

(57) ABSTRACT

A thin absorbent patch, similar to an incontinence pad or guard is disclosed to protect underwear from the leakage of bodily discharges of boys and men. The flexible absorbent article will protect boys and men's underwear from stains caused by excess urine, sexually transmitted diseases, semen and other discharges from the male genitalia. The flexible absorbent article comprises of a fluid-impermeable cover, a fluid-impermeable deflecting baffle and an engulfing absorbent betwixt the cover and the baffle. The flexible absorbent article also comprises of a garment adhesive that will be protected from contamination by peel or wax paper.

2 Claims, 2 Drawing Sheets

PROTEX PATCH FOR BOYS AND MEN

CROSS REFERENCE TO RELATED APPLICATIONS

This application claims the benefit of Provisional Patent Application Ser. No. 60/124,353 filed on Mar. 5, 1999.

BACKGROUND OF THE INVENTION

This invention relates to a thin absorbent patch for male underwear. Specifically, the invention relates to a method and apparatus for keeping male underwear free from stains.

The general object of this invention is to provide a thin absorbent patch for consuming and retaining discharges from boys and men. These discharges are excess urine, discharges caused by sexually transmitted diseases, semen and other discharges, the thin absorbent patch will protect boys and men's underwear from being stained.

The invention is generally related to a flexible absorbent article for absorbing and retaining male discharges. The flexible absorbent article is not a full diaper, pad or pouch for boys and men of all ages. The flexible absorbent article was created to protect boys and men's underwear from stains caused by excess urine, sexually transmitted disease, semen and other discharges from the male genitalia. The flexible absorbent article is not an incontinence product; it is a product for the everyday boy and man.

The reason why the flexible absorbent article was created has been overlooked since the beginning of time. Underwear is the foundation of fashion, underwear is normally the first piece of clothing that is put on, therefore, it is the most important part of fashion. The rest of the clothing is put on top of the underwear, however, there is no protection for the everyday boy and man. Every time a boy or a man goes to the bathroom there is excess urine. Not all boys and men are incontinent, however, these drips are inevitable. In order for men to keep dry, there are men that wipe themselves and place toilet tissue in their underwear to protect their underwear from stains. This is not saying that they are incontinent but the laws of physics and science do not allow anything to go from wet to instantly dry. Specifically, the male penis is not dry after voiding liquid waste from the penis.

The normal color of urine is amber or pale yellow, this color changes with the types of vitamins or medicine that an individual is taking. People now more than ever are health conscience and taking vitamins, which is changing the color of their urine.

The patch was further created to protect boys and men's underwear from stains caused by sexually transmitted diseases. In the U.S. one out of four adults have a sexually transmitted disease and every year there are approximately twelve million new cases. With the population of our country at nearly three million people, approximately fifty to seventy-five million adults are affected by sexually transmitted diseases. Half of these people are men. Consequently, between twenty-five to thirty-seven and one-half million men are effected by sexually transmitted diseases. Chlamydia accounts for forty percent of nongonnococal urethritis. Nongonnococal urethritis is an infection of the urethra that carries urine from the bladder. The symptoms of chlamydia are similar to the symptoms of gonorrhea. The symptoms include yellow or white mucupurulent. Mucupurulent is mucus and pus discharge from the penis, the need to urinate more and/or burning or painful discharging of urine. With all of these men being affected and these symptoms a device that will absorb these infectious discharges is needed. Touching ones clothing and bodily fluids can spread some sexually transmitted diseases. Conventional washing of the underwear does not infallibly sanitize underwear because if the underwear is not washed properly bacteria can spread from person to person.

The flexible absorbent article was also created to protect boys and men's underwear that suffer from diabetes. The type of diabetes that most boys and men suffer from is called diabetes insipidus, which is a disorder of the water metabolism. Diabetes insipidus results from a deficiency of a hormone called ADH. ADH is the hormone that lessens urine secretion. Excessive consumption of fluids (polyipsia) and excessive urine production (polyuria) characterize this particular type of diabetes, boys and men that suffer from this type of diabetes urinate from four to sixteen quarts of urine on a daily basis. In some extreme cases the individual can urinate up to thirty quarts a day. The stains that are being caused by these drips of urine are undoubtedly causing stains in the individual's underwear.

The article was also created to protect boys and men's underwear from semen before and after sex. This opal colored and viscid or sticky fluid solidifies once it settles and will stain boys and men's underwear.

SUMMARY OF THE INVENTION

Another object of this invention is to provide a thin absorbent article for boys and men that has a thickness of one-sixteenth of an inch or less.

Another object of this invention is to provide a thin absorbent patch that is created from a multi-layer of fine fluff, pulp, etc.

Yet another object of this invention is to provide an alternative and less expensive version of protection from stains caused by excess urine, sexually transmitted diseases and semen for boys and men's underwear.

An additional advantage of the flexible absorbent article is that the thin absorbent article provides adequate time and privacy to void urine. Adequate time and privacy are important to most North American boys. North American boys expect private toilet facilities, whereas European cultures accept communal toilet facilities. When a boy goes to the bathroom to void urine the post void time period may be the most time consuming because after a boy is done voiding there is always excess urine that remains in the urinary tract that will dribble out on its own. With the patch in place the boy may go to the bathroom and not have to worry about the excess urine creating stains in his underwear or clothing. The amount of times a boy goes to the bathroom will depend on how much and what he has had to drink and his surroundings. The boy, because of time constraints in school, church and other places tends to rush when he is voiding urine. By the boy rushing and having time constraints, the boy is likely to have an excess amount of urine after voiding that will stain his underwear. With the patch in place time will be saved because the boy will be able to void and not feel wet and embarrassed when he is done voiding.

Similar to North American boys, privacy and adequate time to void are very important to most North American men. North Americans expect toilet facilities to be private whereas European cultures accept communal toilet facilities. Working conditions also influence the time of voiding. When a man goes to the bathroom to void urine, the most time consuming part of the process is generally the post void time period. The amount of times a man goes to the bathroom depends on what he drinks and eats (coffee, tea cocoa and drinks with caffeine increases the formation and excretion of urine). Foods such as fruits and vegetables also increase a man's urine production if their intake of liquid is high.

There is always excess urine in a man's urinary tract in the post void time period. This is not to say that every man is incontinent but it is scientifically and physically impossible to go from being wet to instantly dry. No matter how long the man shakes, taps or wiggles his penis this excess urine will come out on its own. The article will allow men to go to the bathroom and void without being concerned about standing and waiting for the last drip to come out of the penis. Now boys and men will be able to void and permit the flexible absorbent patch to absorb excess urine during the post void time period.

The patch will save time in an additional manner when laundering men's undergarments. Stains that are caused by excess urine, discharges from sexually transmitted diseases, semen and other discharges are present on a male's underwear and need attention during the laundering process. The patch will save time by allowing for the completion of all of the laundry at one time and not soaking underwear in bleach or other chemicals to breakdown stains. The flexible absorbent patch will absorb these stains caused by excess urine, discharged from sexually transmitted diseases, semen and other discharges before they are created on a man's underwear and help the underwear last longer.

The deficiency that is displayed by absorbent articles for boys and men is that the articles are relatively inflexible and can feel unpleasant when positioned between the users thighs. Boys and men are not accustomed to wearing anything between their thighs. It is preferred that these articles are flexible and thin so the article will be comfortable to wear.

The flexible absorbent article contains a multi-layered absorbent structure that absorbs and contains excess urine, discharges caused by sexually transmitted diseases, semen and other discharges from the male genitalia.

Other objects and advantages of the present invention will become more apparent to those skilled in the art of absorbent products in view of the following descriptions and accompanying drawings.

DETAILED DESCRIPTION OF THE INVENTION

Figure 2:
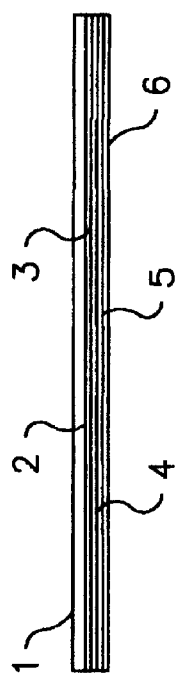
FIG. 2 shows a cross sectional view of the flexible absorbent article.
Figure 1:
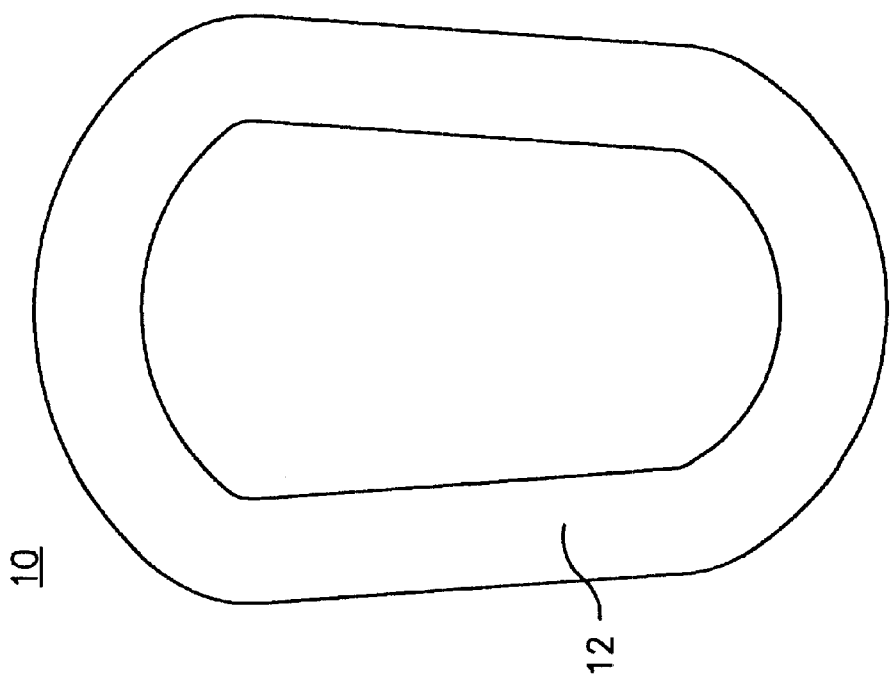
FIG. 1 shows a front view of the flexible absorbent article having a multi-layered infrastructure.
Figure 3:
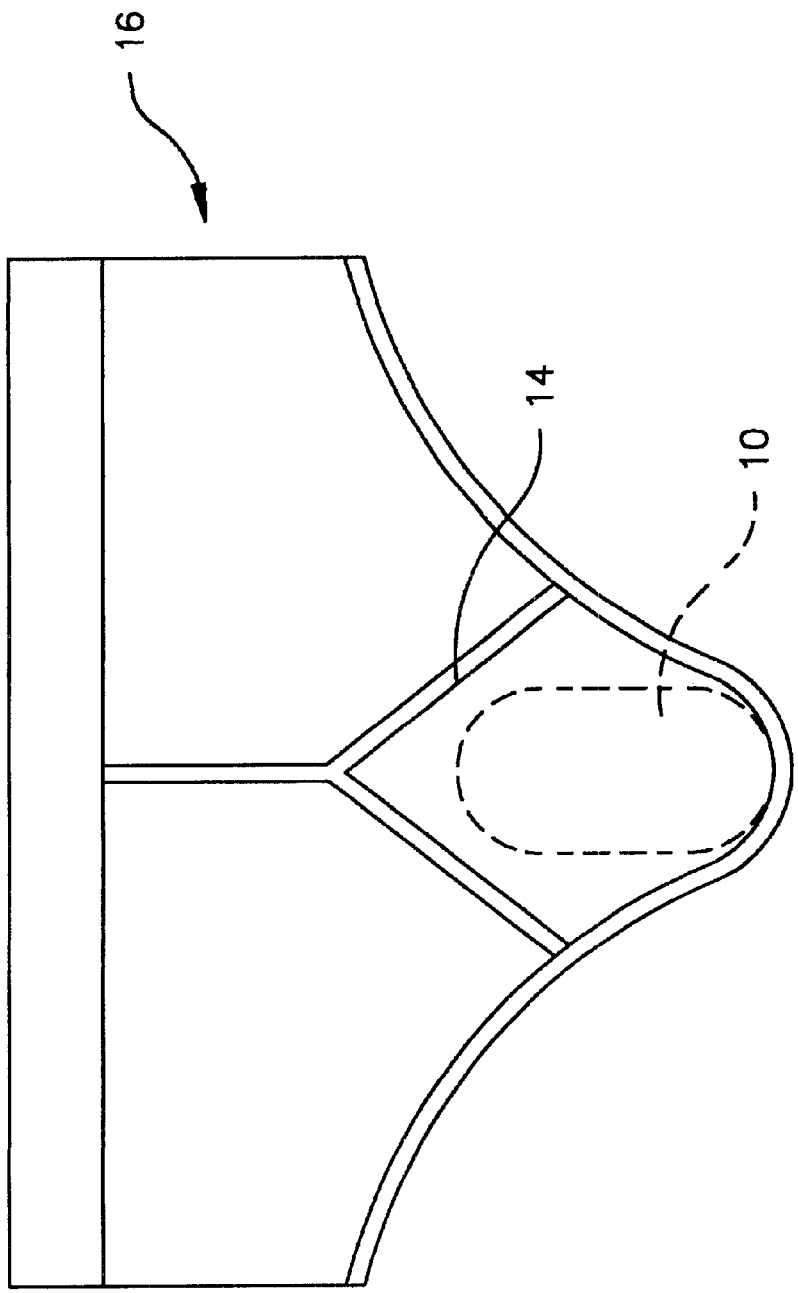
FIG. 3 shows a front view of the flexible absorbent article secured to a male undergarment.

Referring to FIG. 2, the flexible absorbent article is shown, which is smaller and thinner than an incontinence pad, pouch, guard or diaper. Although the flexible absorbent article will be described with reference to incontinence pads, pouches and guards it will encompass shields and diapers. Nevertheless, the flexible absorbent article should be used with underwear and can be used with shields and undergarments.

The flexible absorbent article is a product having an overall thickness of no more than $1/16$ of an inch thick. Almost all pads and pouches are normally rectangular shaped with rounded ends, have a shape similar to an hourglass or are oval shaped. The flexible absorbent article 10 includes a fluid-permneable covering 1 and a fluid impermeable baffle 4 engulfing absorbent 2 and 3 between the cover 1 and baffle 4. The cover 1 is designed to contact the external urethral orifice or the opening of the head of the penis. The cover 1 can be constructed of non-woven or woven materials that are readily permeated by body fluids. The cover 1 can also be either natural pressed cotton or man made materials, such as polypropylene, polyethylene and netted materials. The preferred cover 1 material is a composite of a thermoplastic film positioned above a non-woven fabric material. The composite material exhibits a relaxed and soft outer surface that is not irritating to boys and men's skin.

The presence of pores in the corporeal cover 1 allows excess urine, discharges caused by sexually transmitted diseases, semen and other discharges to move quickly into the absorbent 2 and 3 and allows the flexible absorbent article 10 to be very comforting to wear. By permitting the excess urine, discharges caused by sexually transmitted diseases, semen and other discharges to move quickly through the cover 1 the flexible absorbent article 10 will stay drier longer along with the body of the wearer. This will happen because the absorbent 2 and 3 draws the moisture away from the cover 1 and the body.

The fluid impermeable baffle 4 allows the passage of air out of the flexible absorbent article 10, while obstructing the passage of excess urine, discharges causes by sexually transmitted diseases, semen and other discharges. The pitied material for the baffle 4 is polyethylene or polypropylene as with the cover 1. The preferred material for the cover 1 and baffle 4 is polyethylene film.

The baffle 4 can be cut to a size and appearance, which will make it coextensive with the cover 1. In addition, the baffle 4 can be bonded to form a sealed flexible absorbent article 10. It is also possible to wrap the cover 1 around the absorbent 2 and 3 and bond a periphery of the baffle 4 to the cover 1. Bonding the periphery of the baffle 4 and the cover 1 creates a peripheral rim 12 about a periphery of the flexible absorbent article 10 with the absorbent 2 and 3 positioned radially and inwardly of the rim 12 adjacent a geometric center of the article 10.

The cover 1 and the baffle 4 will contain the absorbent 2 and 3 between them. However, the baffle 4 does not have to be directly bonded to the cover 1. The absorbent 2 and 3 is constantly positioned between the cover 1 and the baffle 4.

The flexible absorbent article 10 will also have a garment adhesive 5 on the bottom of the baffle 4 generally covering the entire baffle 4. The garment adhesives 5 function is to allow the flexible absorbent article 10 to adhere to the inner crotch portion of boys and men's underwear 16 or other types of undergarments. The garment adhesive 5 permits the flexible absorbent article 10 to remain aligned to the head of their penis. The garment adhesive 5 is obtainable from National Starch and Chemical Co. located in Bridgewater, N.J. 08807.

In order to safeguard the garment adhesive 5 from contamination prior to use, the garment adhesives 5 are preserved by a releasable peel paper 6. The peel paper 6 can be a white Kraft paper or light wax paper coated on one side so that the flexible absorbent article 10 can be released from the peel paper 6. The peel paper 6 was created to be taken off by the boy or man at the moment before they attach the flexible absorbent article 10 to the inner crotch portion of their undergarment 16. The flexible absorbent article 10 is positioned adjacent a fly 14 of a male users undergarment 16 in a use position. Positioning the article 10 in the above described manner permits the male user to absorb post void male human waste into the article 10 in the use position because the article 10 is adjacent the users penis.

We claim:

1. A method of absorbing post void male human liquid waste to prevent the waste from contacting a male undergarment including the steps of:

a) releasably securing a generally planar post void liquid waste absorbing article having a first side and a second side wherein the entire first side is in facing engagement with an inner crotch portion of the male undergarment having a fly such that when the male undergarment is worn by a male user the head of the user's penis is adjacent the article to absorb and post void liquid waste which may exude from the penis;

b) voiding any liquid waste from the male user's penis into a human liquid waste receptacle; and c) positioning the undergarment on the user after voiding any liquid waste such that the head of the user's penis is adjacent the second side of the article to absorb any post void liquid waste which may exude from the penis.

2. The method of absorbing post void male human liquid waste of claim 1 wherein step (a) comprises removing a peel paper covering the first side of the article having a releasable adhesive disposed thereon.

\* \* \* \* \*